(12) United States Patent
Hessam

(10) Patent No.: US 12,246,164 B2
(45) Date of Patent: *Mar. 11, 2025

(54) ASSEMBLY FOR DISPENSING A LIQUID COMPRISING AN APPARATUS AND A COMPRESSIBLE BAG

(71) Applicant: OSAA INNOVATION APS, Hillerod (DK)

(72) Inventor: Abdullah Ahmed Hessam, Hillerod (DK)

(*) Notice: Subject to any disclaimer, the term of this patent is extended or adjusted under 35 U.S.C. 154(b) by 0 days.

This patent is subject to a terminal disclaimer.

(21) Appl. No.: 18/491,878

(22) Filed: Oct. 23, 2023

(65) Prior Publication Data

US 2024/0050653 A1   Feb. 15, 2024

Related U.S. Application Data

(63) Continuation of application No. 16/758,587, filed as application No. PCT/DK2018/050271 on Oct. 25, 2018, now Pat. No. 11,826,544.

(30) Foreign Application Priority Data

Oct. 26, 2017  (DK) .......................... PA 2017 00605

(51) Int. Cl.
*A61M 5/148*        (2006.01)
*A61M 5/172*        (2006.01)
(Continued)

(52) U.S. Cl.
CPC ............ *A61M 5/148* (2013.01); *A61M 5/172* (2013.01); *A61M 39/28* (2013.01);
(Continued)

(58) Field of Classification Search
CPC .......... A61M 5/14232; A61M 5/14244; A61M 5/148; A61M 2005/14506
See application file for complete search history.

(56) References Cited

U.S. PATENT DOCUMENTS 1,556,437 A   10/1925  Granger
1,660,035 A   2/1928   Fitch
(Continued)

FOREIGN PATENT DOCUMENTS

FR    2887458 A1    12/2006
GB    2 204 797 A   11/1988
(Continued)

OTHER PUBLICATIONS

International Search Report for PCT/DK2018/050271 dated Jan. 3, 2019.
(Continued)

*Primary Examiner* — Jenna Zhang
(74) *Attorney, Agent, or Firm* — Chrisman Gallo Tochtrop LLC

(57) ABSTRACT

The application discloses an assembly including a compressible bag and an apparatus for dispensing a liquid from a bag. The apparatus includes a housing with a dispensing end and an opposite rear end, a bottom part and top part and two side parts. A roller arrangement and a pair of steering tracks are mounted in a track length direction on the side parts, and the roller arrangement includes at least a front roller adapted to roll from the rear end towards the dispensing end. The surface of the roller is adapted for engagement with the compressible bag placed on the bottom part, and a gap is provided between the bottom part and the surface of the front roller, the gap being in the range of 2 to 10 mm where the surface of the front roller is closest to the bottom part.

18 Claims, 13 Drawing Sheets

(51) Int. Cl.
*A61M 39/28* (2006.01)
*A61M 5/145* (2006.01)
*B67D 1/00* (2006.01)
*B67D 7/02* (2010.01)

(52) U.S. Cl.
CPC .............. *A61M 2005/14506* (2013.01); *A61M 2205/36* (2013.01); *B67D 1/0001* (2013.01); *B67D 7/0216* (2013.01)

(56) References Cited

U.S. PATENT DOCUMENTS

| | | | |
|---|---|---|---|
| 2,570,755 | A | 10/1951 | Booth |
| 2,837,243 | A | 6/1958 | Zebnik |
| 3,151,616 | A | 10/1964 | Selfon |
| 3,647,117 | A | 3/1972 | Hargest |
| 3,853,243 | A | 12/1974 | Forman |
| 4,044,764 | A | 8/1977 | Szabo et al. |
| 4,223,809 | A | 9/1980 | Martin |
| 4,285,492 | A | 8/1981 | Bujan |
| 4,331,265 | A | 5/1982 | Warlick |
| 4,575,375 | A | 3/1986 | Kozam |
| 4,805,805 | A | 2/1989 | Ocheskey |
| 4,850,971 | A * | 7/1989 | Colvin ................ A61M 5/148 222/100 |
| 5,211,626 | A * | 5/1993 | Frank .................... G01F 1/7044 604/122 |
| 5,692,645 | A | 12/1997 | Ryu |
| 6,194,420 | B1 * | 2/2001 | Lang ....................... A61P 35/02 514/266.4 |
| 6,196,420 | B1 * | 3/2001 | Gutierrez ............ B67D 1/0001 222/101 |
| 6,669,668 | B1 * | 12/2003 | Kleeman ............... A61M 5/148 222/401 |
| 6,726,655 | B1 * | 4/2004 | Lieberman ........... A61M 5/145 604/131 |
| 6,968,977 | B1 | 11/2005 | Beene |
| 8,550,301 | B2 | 10/2013 | Szymanski |
| D847,209 | S | 4/2019 | Hessam |
| 10,604,397 | B2 | 3/2020 | Sa |
| 2002/0092879 | A1 * | 7/2002 | Chrisman ............ B67D 7/0216 222/504 |
| 2002/0123741 | A1 | 9/2002 | Rake |
| 2003/0098316 | A1 * | 5/2003 | Bochno .............. B65D 81/3261 222/101 |
| 2005/0177136 | A1 | 8/2005 | Miller |
| 2008/0149664 | A1 | 6/2008 | Schroeder et al. |
| 2008/0314923 | A1 | 12/2008 | Faller et al. |
| 2010/0108717 | A1 * | 5/2010 | Szymanski ............ B65D 35/34 222/100 |
| 2010/0137808 | A1 | 6/2010 | Wilmot et al. |
| 2010/0137832 | A1 * | 6/2010 | Mathews .............. A61M 5/2459 604/138 |
| 2011/0024464 | A1 | 2/2011 | Jaouen |
| 2014/0008390 | A1 * | 1/2014 | Burke ................. B67D 7/0216 222/101 |
| 2015/0018765 | A1 | 1/2015 | Wont et al. |
| 2017/0119958 | A1 | 5/2017 | Hessam |
| 2019/0209774 | A1 * | 7/2019 | Schabbach ........ A61M 5/14232 |
| 2024/0189570 | A1 | 6/2024 | Hessam |

FOREIGN PATENT DOCUMENTS

| | | | |
|---|---|---|---|
| JP | 50-7875 | | 3/1975 |
| JP | 2016158932 | A | 9/2016 |
| RU | 2451633 | C2 | 6/2011 |
| RU | 2493881 | C2 | 1/2013 |
| WO | 01/17892 | A2 | 3/2001 |
| WO | WO-2010068415 | A1 * | 6/2010 ............ A61M 5/002 |
| WO | 2016192728 | A1 | 12/2016 |
| WO | 2019/080982 | A1 | 5/2019 |
| WO | 2019/145004 | A1 | 8/2019 |

OTHER PUBLICATIONS

Danish Search Report for PA 2017 00605 dated Apr. 4, 2018.
Supplementary European Search Report for European application No. EP 18 87 0552.9 dated Jun. 22, 2021.
Eurasian Patent Office Examination Report, issued May 23, 2024, 202490138.

* cited by examiner

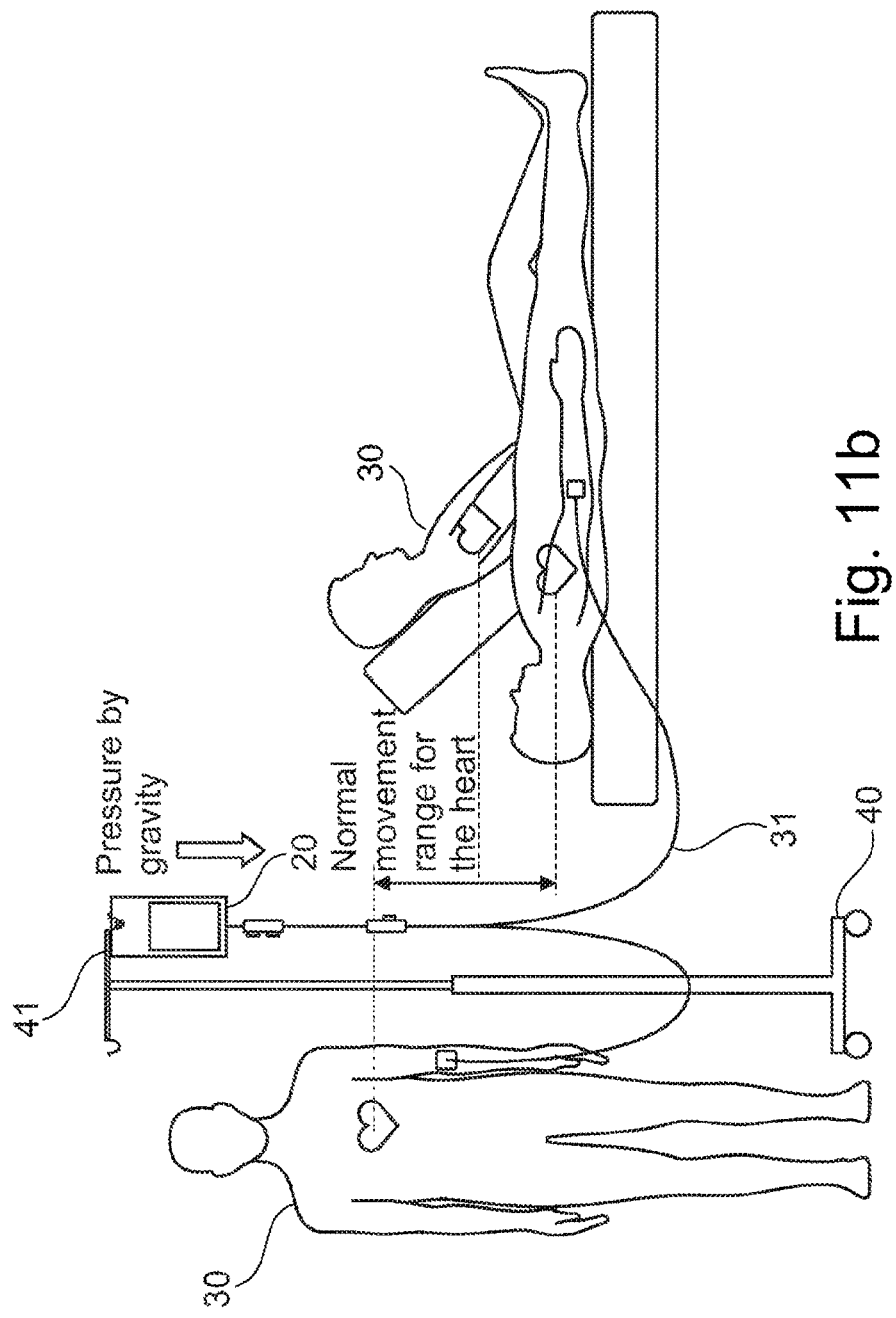

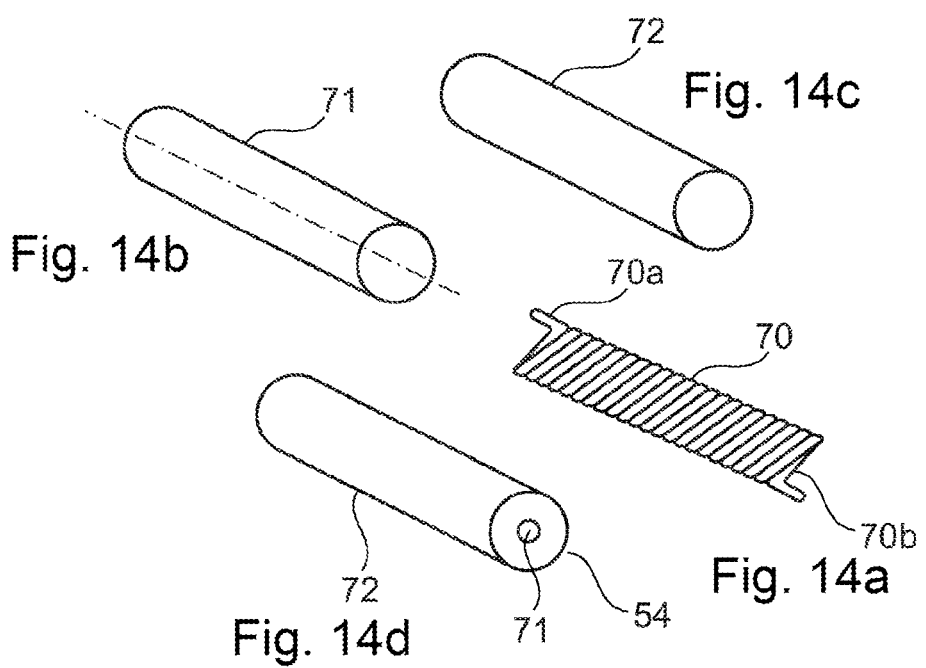

ASSEMBLY FOR DISPENSING A LIQUID COMPRISING AN APPARATUS AND A COMPRESSIBLE BAG

CROSS-REFERENCE TO RELATED APPLICATIONS

This application is a continuation of U.S. application Ser. No. 16/758,587, filed on Apr. 23, 2020, which was a national stage entry of PCT/DK2018/050271, filed Oct. 25, 2018, which claimed priority to Denmark application no. PA 2017 00605, filed Oct. 26, 2017, the entire disclosures of which are incorporated herein by reference.

FIELD OF THE INVENTION

The present invention relates to an assembly comprising a compressible bag and an apparatus for dispensing a liquid from the compressible bag for intravenous infusion of liquid or medication in accordance with a predetermined medical therapy.

BACKGROUND OF THE INVENTION

Patients are often, during hospitalization, getting IV treatment in which they receive liquid and medicine into a vein. It is necessary to elevate the IV bag with liquid and medicine, so the liquid can flow into the vein. For IV treatments such as these IV poles are the most commonly used tools.

IV treatments and IV poles are a significant part of both patients and the healthcare staffs everyday life in many different departments of hospitals.

The disadvantage with the IV pole occurs when nurses and paramedics have to mobilize patients. It often happens that the hospital staff has to allocate additional resources to mobilize patients.

Furthermore the IV poles occupies a lot of space in the wards and causes the staff poor working conditions due to the fact that they are either in unpleasant working positions or have to adjust the IV poles height to cause the liquid to run faster.

Patients who are dependent of an IV pole may also increase problems with coordination among interdisciplinary staff such as nurses, occupational therapists and physiotherapists at the hospitals. Waiting time can occur, if per example a patient must retrain and at the same time complete an IV treatment.

Another frequent issue hospitals have, is that there is lack of IV poles with wheels. This means that patients are limited in their activities and will therefore need to remain in bed because of their dependence of the IV pole. It is therefore not unusual, that patients are kept unnecessary long time in bed, which again can lead to unnecessary immobilization and increase the risk of bedsores.

Furthermore, IV poles reduce opportunities for children to participate in games and other activities due to dependence of IV poles.

Initiation of births frequently takes place while a pregnant woman is given IV treatment. In this situation, mobilization of the pregnant would be an absolute advantage, because she then would be able to move around freely until the birth has really started.

In acute accidents or treatment of patients outside hospitals and ambulance, it is often required that a person acts as an IV pole.

There have been many attempts to provide a bag pump, which does not require a pole.

Smiths Medical, Care Fusion, Baxter and Micrel produces electronic infusion pumps that can make patients independent of the IV pole. Such electronic infusion pumps are however relative expensive.

U.S. Pat. No. 4,850,971 describes an infusion pump utilizing a linear roller driven by a one or more constant force springs in combination with changeable flow regulating needles to provide a constant flow, gravity independent device. The constant spring springs comprises a coil type that is mounted to a storage drum and an end of the coil springs are attached to a plate such that when the drum is pulled away from the plate the spring is unrolled. In use the bag is rolled onto the drum between windings of the coil spring.

U.S. Pat. No. 6,669,668 discloses a medication delivery pump that is configured to administer an infusion therapy using a medication delivery container. Medications in a flexible bag are expelled from the bag and delivered to an infusion site. A fluid delivery pump have a constant force spring and a mechanical timer. The constant force spring is configured to compress a flexible fluid container. The mechanical timer assembly is coupled to the constant force spring and limits the maximum rate at which the spring compresses the fluid container.

It has been found that during the dispensing of liquid from a bag some curling and shrinkage of the bag frequently appears. The curling and shrinkage of the bag may cause that it is not possible to achieve a satisfactory emptying of the bag.

BRIEF SUMMARY OF THE INVENTION

An object of the present invention is to provide an apparatus for dispensing a liquid from a compressible bag in which the risk of curling and shrinkage of the bag during dispensing is reduced.

A further object of the present invention is to provide an apparatus for dispensing a liquid from a compressible bag with high reliability and control of the amount of liquid dispensed.

In an embodiment it is an object to provide an apparatus for dispensing a liquid from a compressible bag in which the compressible bag may be emptied to a preselected stage, such as fully emptied.

This and other objects have been solved by the invention or embodiments thereof as defined in the claims or as described herein below.

It has been found that the invention or embodiments thereof have a number of additional advantages, which will be clear to the skilled person from the following description.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

The term "substantially" should herein be taken to mean that ordinary product variances and tolerances are comprised.

Throughout the description or claims, the singular encompasses the plural unless otherwise specified or required by the context.

All features of the inventions and embodiments of the invention as described herein including ranges and preferred ranges may be combined in various ways within the scope of the invention, unless there are specific reasons not to combine such features.

The invention is defined in claim 1.

The present invention relates to an assembly comprising a compressible bag and an apparatus for dispensing a liquid from the compressible bag, where the apparatus comprises a housing with a dispensing end and an opposite rear end, a bottom part and top part and two side parts. A roller arrangement and a pair of steering tracks are mounted in a track length direction on the side parts, and the roller arrangement comprises at least a front roller adapted to roll from the rear end towards the dispensing end wherein the surface of the roller is adapted for engagement with a compressible bag placed on the bottom part and wherein a gap is provided between the bottom part and the surface of the front roller, the gap being in the range of 2 to 10 mm where the surface of the front roller is closest to the bottom part.

Thus, the apparatus is suitable for dispensing a liquid to a person e.g. as intravenous treatment. The liquid may e.g. be water, water comprising salt and/or sugar, a liquid comprising a medical product or a liquid containing blood or blood plasma.

In an embodiment the apparatus comprises a housing which may be a box-like housing with a dispensing end at a front wall and a rear end at the rear wall, a bottom part adapted to support the compressible bag and top part adapted for closing and opening of the housing and two side parts forming the side walls of the box. The front wall constituting the dispensing end has at least one opening allowing dispensing means like one or more tubes from the compressible bag to pass through.

The front wall, the rear wall, the bottom part, the top part and the two side parts forming the side walls of the box may be substantially planar and be substantially perpendicular to each other, however, the may also be curved and form an angle different from 90 degrees with each other.

The bottom part is adapted to support the compressible bag and is advantageously essentially planar. The bottom part may advantageously interconnect the rear wall and the front wall and also the two opposing side walls.

The top part may comprise two attached walls, which are substantially parallel with the side walls and overlays with the side walls when the housing is closed.

The housing is preferably manufactured from rigid durable material such as metallic or plastic material.

Moreover, due the special feature of providing a gap between the bottom part and the surface of the front roller it has surprisingly been found that this is able to reduce the compressible bag's tendency of curling and shrinkage during the dispensing process. The roller arrangement may comprise at least one follower roller following the front roller, which in combination with the gap provides a very good effect in respect of reducing of curling and shrinkage of the compressible bag during the dispensing process.

It has also been found that the invention has the advantage that back flow of liquid in the compressible bag is reduced.

When a gap is provided between the bottom part and the front roller, it should preferably be ensured that the gap is larger than the wall thickness of the compressible bag, i.e. the thickness of the compressible bag when it is empty and contains no liquid and lies flat on a surface. Preferably, the gap is at least 1 mm, such as at least 1.5 mm, such as at least 2 mm larger than the wall thickness of the compressible bag. The gap may be up to about 9.9 mm, such as up to 10.0 mm larger than the wall thickness of the compressible bag.

In an embodiment of the apparatus, the roller arrangement is activated by a spring arrangement. A spring arrangement can be provided easy and cost-effective.

In an embodiment of the apparatus according to the invention, the roller arrangement is activated and/or driven by an electric motor. The electric motor may be built in the front roller or mounted exterior to the rollers. In the latter case, the motion of the roller system can be affected by a pulling or drawing device.

In an embodiment the compressible bag is attached to the roller when the roller arrangement is constituted by one front roller. When the front roller is the only roller in the roller arrangement it has been to be very efficient that the compressible bag is rolled up on the front roller during the dispensing process. To facilitate this, it is an advantage to attach the rear end of the compressible bag to the roller. The compressible bag can be attached by means of e.g. tape or squeezing means.

In an embodiment the compressible bag is attached to the bottom part when the roller arrangement comprise at front roller and at least one follower roller. The compressible bag can be attached by means of e.g. tape or squeezing means. The attachment will be described in more details below.

In an embodiment the apparatus comprises a housing with a dispensing end and an opposite rear end, a bottom part and top part and two side parts, a spring activated roller arrangement and a pair of steering tracks mounted in a track length direction on said side parts. The spring activated roller arrangement comprises a front roller and at least one follower roller and at least one spring operatively engaged with, operatively connected to or integrated with at least one front roller axle, which roller axle forming part of the front roller or being surrounded by a hub of the front roller, such that displacing the front roller axle along the tracks length direction away from the dispensing end charges the spring. The spring being engaged with the pair of tracks to hold the front roller axle perpendicular to the pair of tracks, and wherein the front roller has a roller body with an outer roller surface adapted for directly engage with a compressible bag placed on the bottom part as the loaded spring moves the front roller of the roller arrangement over the bottom part and the compressible bag towards the dispensing end.

The compressible bag is preferably a compressible bag for IV treatment and when such a bag comprising liquid is placed on the bottom part of the housing and the spring activated roller arrangement is activated, this will cause the front roller and the at least one follower roller to roll over the bag and effect that the liquid is squeezed out of the bag via a dispensing tube attached to the bag.

Thus, a liquid may be dispensed from the compressible bag e.g. dispensed to a patient. It has been found that the apparatus is highly reliable and the risk of damaging the bag during dispensing is very low. Advantageously the contact between the one or more rollers and the bag is a firm contact essentially without frictional force but a simple rolling of the rollers over the bag while the one or more rollers is pressing the bag towards the bottom part of the housing, preferably in an embodiment with more rollers without the bag being removed from the bottom part. Thus, the apparatus may ensure a simple and safe dispensing of the liquid.

In an embodiment the bag comprises a bag fastener for fastening the bag in the housing. The bag fastener may for example be or comprise a hook, a button, a buckle and/or Velcro. The bag fastener is advantageously positioned at the bottom part closer to the rear wall than to the dispensing end, such as at or near the rear wall.

In an embodiment of the roller arrangement, the front roller is closer to the dispensing end than the follower roller(s) when the spring is unloaded. Thus the front roller may press liquid out of the bag and the follower roller(s) may ensure that liquid or air does not flow backwards in the bag when the front roller has squeezed the bag. When the spring is unloaded the front roller may be in contact with or close to the dispensing end, e.g. with certain distance from the dispensing end. In an embodiment, the distance may vary within a range from about 0.1 cm to about 10 cm, such from about 0.5 cm to about 7 cm, such as from about 1 cm to about 6 cm.

In an embodiment the front roller and the follower roller(s) are arranged in parallel and interconnected one after the other. Optionally the interconnection comprises a stiff or a flexible chain interconnection or a combination thereof. The interconnection of the roller makes it possible to maintain a predetermined distance between the rollers so the roller are not contacting. If neighboring rollers are contacting, this may disturb the roller function of the roller arrangement, which is undesired.

In an embodiment the distance between two adjacent rollers of the roller arrangement is less than about the average diameter of the adjacent rollers, such as less than about 2 cm, such as less than about 1 cm, or less than about 0.5 cm. The smaller the distance is between two adjacent rollers the better will the roller arrangement function in respect of dispensing fluid from the compressible bag. Where the front roller and the follower roller(s) have flexible interconnection(s), the distance is determined as the distance when the adjacent rollers in question are furthest from each other.

The front roller comprises a roller axle and the spring activated roller arrangement comprises at least one spring operatively engaged with, operatively connected to or integrated with the front roller axle. The front roller axle forms part of the front roller, e.g. by forming the central part of the front roller or being surrounded by a hub of the front roller. The spring used in the spring activated roller arrangement may e.g. be a coil spring, a plate spring, a constant-force spring or a spring device based on hydraulic. The spring activated roller arrangement also comprises means to load the spring and release the spring to move the front roller and the roller arrangement. The spring may also engage with one or more follower rollers of the roller arrangement. The spring and the means for loading and release the spring may be fully or partly located in the steering tracks.

In an embodiment, the apparatus also comprises a timer device, which may serve to release or interrupt the spring force to the roller arrangement. Thus, the dispensing of liquid can appear in a predetermined period. The timer device may be a mechanical or electronic device.

The follower roller(s) is/are adapted for following the front roller, preferably in a predetermined distance, and in an embodiment the at least one follower roller has an outer roller surface and is engaged in said pair of tracks to provide that the outer roller surface of the follower roller is adapted for directly engagement with the compressible bag placed on the bottom part when the loaded spring moves the front roller, and thereby, the follower roller follows the front roller and serves to facilitate the dispensing of the fluid in the compressible bag.

The front roller may have a diameter which is larger than the diameter of the follower rollers, e.g. a diameter which is 1.5 time greater, such as 2 times greater or even 2.5 times greater than the diameter of the follower roller(s). In an embodiment the front roller has a diameter corresponding to the diameter of the at least one follower roller. In this embodiment, it is possible to apply the same types of rollers to the roller arrangement.

In an embodiment, at least one of the rollers in the roller arrangement has a diameter, which is different from the diameters of at least one other of the rollers, preferably the front roller has a diameter which is larger than the follower roller(s). The roller with larger diameter may easier move over a compressible bag containing liquid to be dispensed.

The rollers in the roller arrangement may have a diameter in the range of from about 0.5 cm to about 5 cm, such from about 1 cm to about 3.5 cm.

The apparatus according to the invention comprises in an embodiment at least one follower roller and in an embodiment, the roller arrangement comprises at least 2 follower rollers, such as at least 3 follower rollers, such as from 4 to 50 follower rollers, such as from 5 to 30 follower rollers. A higher number of follower rollers may improve the dispensing quality of the apparatus. However, too many follower rollers may take up excessive space.

In an embodiment of the apparatus, the outer roller surfaces of the front roller and the follower rollers of the roller arrangement do not engage with each other when the roller arrangement is moved over the bottom part and the compressible bag towards the dispensing end. If the outer roller surfaces of two or more rollers are engaged during movement this may cause every second roller to roll in a different direction than the remaining rollers and the effectiveness of the apparatus may be reduced. To obtain an arrangement where the surfaces of the rollers do not engage, the front roller and the follower roller(s) are preferably arranged in parallel and interconnected one after the other. The interconnection may comprises a stiff or a flexible chain interconnection or a combination thereof. The interconnection may be constituted by track elements, which are mounted in the steering tracks in a manner so the track elements can slide in the steering tracks. The track elements may be equipped with attachment means for attachment of the axles of the rollers. The track element makes it possible to mount the rollers with a predetermined distance between them so the surfaces of the rollers are not contacting. Preferably, the rollers are provided with axles which engage with the interconnection and the steering tracks. In case the rollers have different diameters, one or more adaptors may be applied for the interconnection.

Although the rollers in the roller arrangement may have any desired width, the apparatus encompass an embodiment in which the outer roller surfaces of the front roller and the follower rollers of the roller arrangement have a width in the range of from about 5 cm to about 75 cm, such as from about 5 cm to about 50 cm, such as from about 5 cm to about 25 cm, such as from about 5 cm to about 10 cm, such as from about 6 cm to about 8.5 cm. Thus, the apparatus can be provided for standard bags with varying widths, such as compressible bags with width 7.5 cm or 3 inches.

In an embodiment, the outer roller surfaces of the front roller and the follower rollers of the roller arrangement have substantially equal width. This embodiment facilitates the manufacture of the apparatus.

The rollers may e.g. be manufactured from plastic or metallic material or a combination of materials. Thus, the axle and a central part of the rollers may be produced by metallic material, such as stainless steel, and the outer surface by plastic material, e.g. from polymer material. The roller arrangement may also include other parts such as bearings and gear-wheels.

As mentioned the roller arrangement may comprise only one roller, which is normally denoted "front roller". The driving mechanism to move the one or more rollers is normally mounted to affect the front roller. The driving mechanism may be a spring device or an electric motor.

In an embodiment the apparatus preferably comprises a propulsion spring mechanism having a first and a second end. The first end of the propulsion spring mechanism can be fixed to the housing at a position depending on the type of propulsion spring mechanism. The second end of the propulsion spring mechanism is fixed to one or more rollers in the roller arrangement which is adapted to squeeze a compressible bag between the roller and the bottom part by action of the propulsion spring mechanism for thereby dispensing a liquid from the compressible bag e.g. for dispensing the liquid to a patient. It has been found that the apparatus is highly reliable and the risk of damaging the bag during dispensing is very low.

In an embodiment, the type of propulsion spring mechanism is a compression spring mechanism where the propulsion spring mechanism is compressed from its resting position to a loaded condition. In this embodiment, the first end of the propulsion spring mechanism is advantageously fixed to the rear wall.

In an embodiment, the type of propulsion spring mechanism is a tensile spring mechanism where the propulsion spring mechanism is stretched from its resting position to a loaded condition. In this embodiment, the first end of the propulsion spring mechanism is advantageously fixed to the front wall.

In an embodiment, the propulsion spring mechanism is fixed to the rear wall of the bag and the propulsion spring mechanism is a compression spring mechanism, such as a telescopic conveyance mechanism.

In an embodiment, the propulsion spring mechanism comprises at least one spring arranged to provide the propulsion. The spring may be a compression spring or a tensile spring.

The propulsion spring mechanism may comprise two or more springs of same or different type.

As mentioned the spring can be any suitable spring which can be loaded and effect the desired movement or propulsion of the roller arrangement. The roller arrangement may comprise one or more springs, such as two springs and the spring(s) is(are) preferably charged or loaded by pressing the spring in a direction away from the dispensing end. In an embodiment the spring(s) is(are) engaged to or within the steering tracks and the steering tracks serve to control the movement of the spring(s). The spring(s) may e.g. be encapsulated in a tubular member or other guidance means attached to the steering tracks. In an embodiment the spring(s) can be fully or partly integrated in one or more of the rollers, preferably the spring(s) is(are) integrated in the front roller.

In an embodiment, at least a part of the spring is mounted in the rear end of the housing. The spring can be mounted e.g. to the rear wall by any suitable means, such as screws or rivets.

In an embodiment, at least a part of the spring is mounted in the top part of the housing. When the spring is mounted in the top part of the housing it can be necessary to adapt the steering tracks and the guidance means so as to guide the spring to the top part in an appropriate manner.

In an embodiment, at least a part of the spring is mounted below the bottom part of the housing. In such an embodiment the at least a part of spring is guided to a position below the bottom part and attached below the bottom part. In an embodiment, the spring is guided below the bottom part through openings in the bottom part preferably at the rear end. In an embodiment, the spring is guided below the bottom part through openings in the bottom part preferably at the dispensing end. The housing may comprise an additional bottom to cover the mounting of the spring to the bottom part.

The steering tracks are generally mounted on the side parts of the housing, however, in an embodiment at least a part of the steering tracks can be mounted on other parts of the housing.

In an embodiment, a part of the steering tracks is mounted in the top part of the housing. In this embodiment, the part of the steering tracks which is mounted in the top part may be mounted on side walls attached to the top part and integrated with the top part. The attached side walls are preferably parallel to the side parts of the housing.

In an embodiment, a part of the steering tracks is mounted below the bottom part of the housing. In this embodiment, the steering tracks are lead through openings in the bottom of the housing. The housing may comprise an additional bottom to cover the steering tracks below the bottom part.

In particular, when a part of the steering tracks is mounted in the top part a certain flexibility of the steering tracks may be required and in an embodiment of the apparatus at least at part of the steering tracks are flexible.

To allow access to the interior of the housing for mounting or removal of a compressible bag the top part is partly or fully releasable.

In an embodiment the top part is mounted on a hinge allowing the top part to open and allow access to the internal part of the housing, e.g. for replacing a compressible bag.

When the roller arrangement only comprise the front roller and the compressible bag is rolled up on the front roller, the bag may simply be un-rolled from the front roller and replaced by another bag.

When the roller arrangement comprise more rollers the procedure is different. To replace a compressible bag from the bottom part of the housing it is necessary to withdraw the rollers from the bottom part or at least from a major part of the bottom part whereby the compressible bag can be released from the bottom part. The movement and force required to withdraw the rollers may also be utilized to charge or load the spring.

In an embodiment the spring(s) in the roller arrangement is(are) charged or loaded when the rollers are withdrawn from the bottom part.

In an embodiment, the spring is at least partly charged or loaded by opening the top part of the housing.

In an embodiment of apparatus according to the invention, the rollers are at least partly withdrawn from the bottom part when the top part is opened. Thus, a withdrawal of the rollers during opening of the top part may be achieved whereby the compressible bag easily can be replaced.

The invention also comprises an embodiment where the apparatus comprises a handle for loading the spring and at least partly withdrawing the rollers from the bottom part.

In an embodiment, the apparatus comprises an electronic device for monitoring at least one condition of a compressible bag arranged on the bottom part of the apparatus, the condition preferably comprises at least one dispensing condition, such as dispensing rate, dispensing status or dispensing time left.

The electronic device may also comprise means for monitoring the temperature of the liquid in the bag and in an embodiment, the apparatus comprises a heating arrangement adapted to heat the liquid in a compressible bag. Thus, the liquid may be kept at a temperature, which is corresponding to or near the temperature of the human body.

In an embodiment, the apparatus comprises a vibrating device. The vibrating device may facilitate dispensing of a liquid, which is viscous.

The apparatus may also be equipped with additional control devices, e.g. an on/off switch to control movement of the spring and the rollers in the roller arrangement and optional a device by which the speed of the rollers over the bottom part can be adjusted.

BRIEF DESCRIPTION OF THE DRAWINGS

The invention will now be described in further details with reference to embodiments and examples shown in the drawing in which:

FIGS. 11a to 11b show intravenous treatment using a pole;
FIGS. 14a to 14d show details of the roller.

The figures are not accurate in every detail but only sketches intended to the show the principles of the invention. Details which are not a part of the invention may have been omitted. In the figures the same reference numbers are used for the same or corresponding parts.

DESCRIPTION OF EXAMPLE EMBODIMENTS

Figure 1:
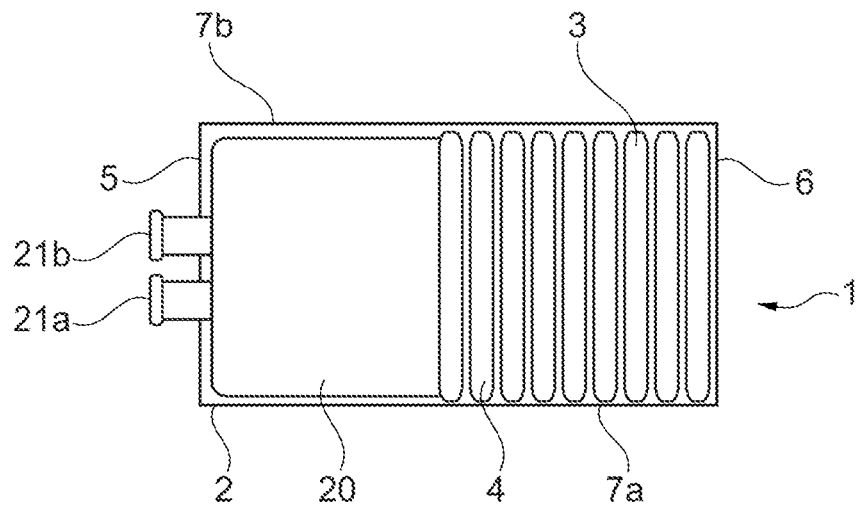
FIG. 1 shows an embodiment of the rollers in the housing.

FIG. 1 shows an embodiment of the apparatus 1 according to the invention and in a simplified manner the roller arrangement in the housing.

The apparatus comprises a housing 2 in which a roller arrangement 3 is arranged. The individual rollers 4 are arranged to be mutual parallel and parallel with the dispensing end 5 and the rear end 6 of the housing.

The rollers 4 are substantially perpendicular to the side parts 7a and 7b of the housing 2.

A flexible bag 20 is placed on the bottom part of the housing and the outlet tubes 21a and 21b are lead through an opening 10 in the dispensing end 5

Figure 2:
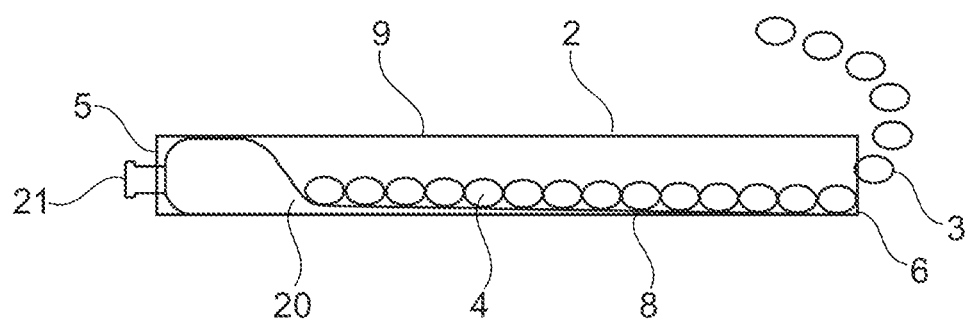
FIG. 2 shows the rollers in the housing seen from the side.

FIG. 2 shows the housing 2 in a side view. The bottom part 8 and the top part 9 can be seen. The rollers 4 are moving over the bottom part 8 and squeeze on the compressible bag 20. The compressible bag 20 comprises a liquid, which is dispensed through the outlet tube 21 at the dispensing end 5. In this illustrative figure the roller arrangement 3 pass through the rear end 6 of the housing 2.

As it can be seen the part of the compressible bag 20 closest to the dispensing end 5 still contains liquid which can be dispensed by the movement of the roller arrangement 3 towards the dispensing end 5.

Figure 3A:
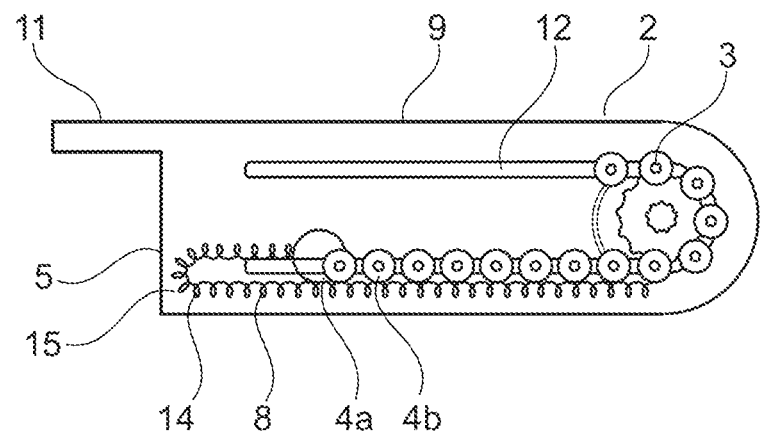
FIGS. 3a and 3b show the housing closed and opened.
Figure 3B:
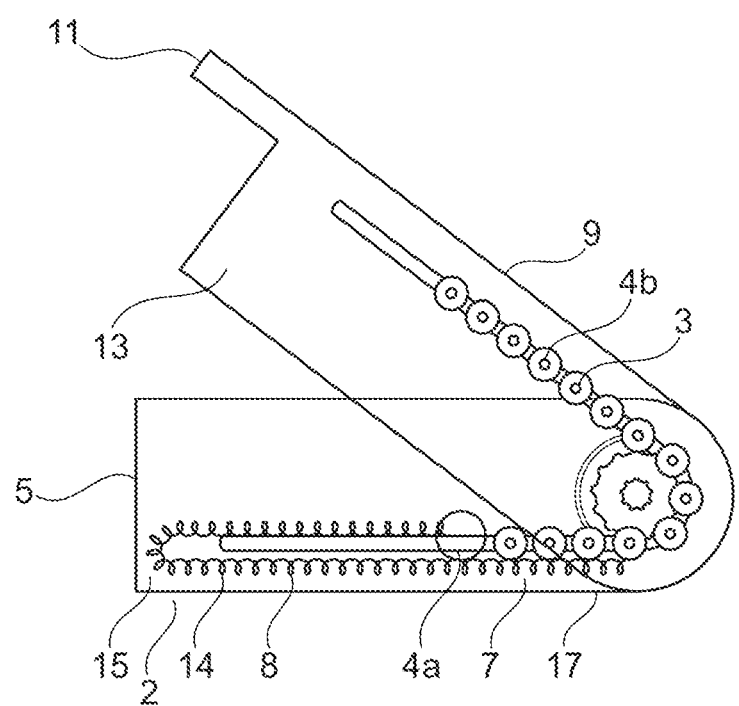

FIGS. 3a and 3b shows an embodiment of an apparatus. FIG. 3a shows a situation where the housing 2 is closed and FIG. 3b shows a situation where the top part 9 is raised by means of a handle 11 and the housing is open.

The steering track 12 is mounted on the side part 7 of the housing and also on a side wall 13 of the top part 9. The side wall 13 is integrated with the top part 9 as seen in FIG. 3b and the side wall 13 is arranged to be parallel with the side part 7 of the housing 2.

The roller arrangement 3 comprises a front roller 4a which has a larger diameter than the follower rollers 4b. An adaptor (not shown) may be used to connect either the axle of the front roller 4a or the follower rollers 4b with steering track 12 and the spring 14. The roller arrangement 3 are caused to move by means of the spring 14 which in this embodiment engage with the front roller 4a and arranged so it able to pull the rollers 4 toward the dispensing end 5 of the housing 2.

The spring 14 is attached below the bottom part 8 and passes through and opening 15 in the bottom part 8 near the dispensing end 5

To control the motion of the roller arrangement 3 when it moves to bottom part 8 from the top part 9 the apparatus comprise a gear wheel 16. The housing 2 also comprises an extra bottom to cover the spring 14 mounted below the bottom part.

Figure 4:
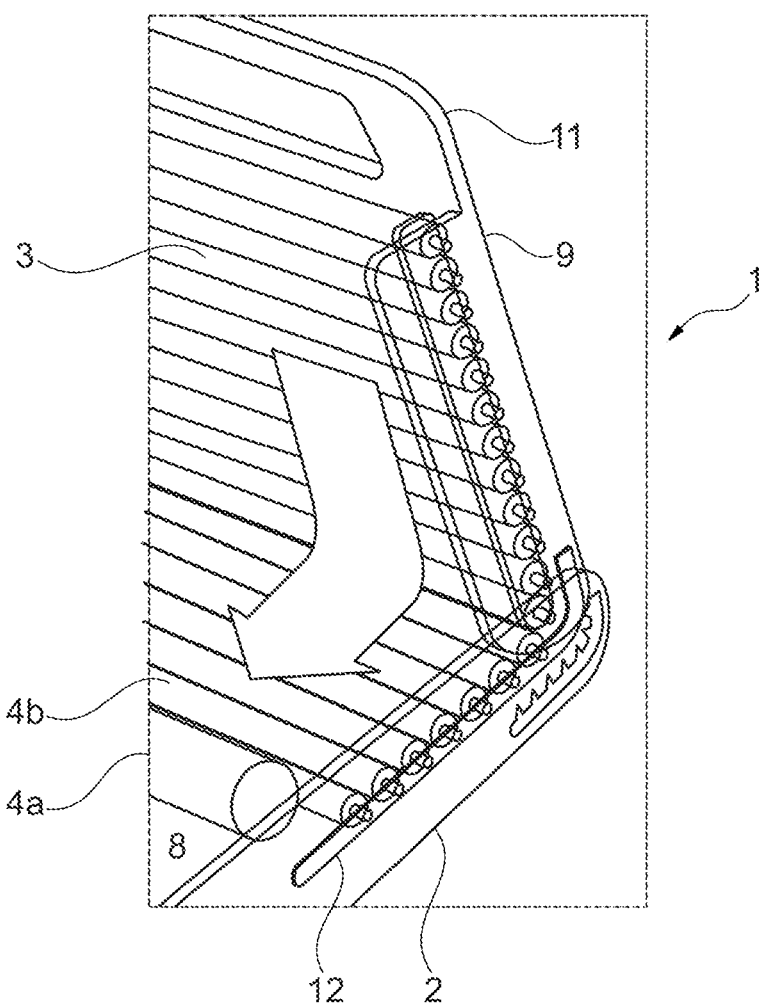
FIG. 4 shows a view of the apparatus depicted in FIGS. 3a and 3b.

FIG. 4 shows a section of the apparatus 1 illustrated in FIGS. 3a and 3b. It can be seen how the rollers 4 are mounted in the steering track 12 and the arrow illustrates how the roller arrangement moves in the apparatus 1 when the spring pulls the rollers towards the dispensing end.

In the FIGS. 3a, 3b and 4 the apparatus 1 is shown without a compressible bag.

The FIGS. 5a to 5d illustrates how the housing can be opened for replacement of a compressible bag and how the top part can function as a lid for the apparatus.

Figure 5A:
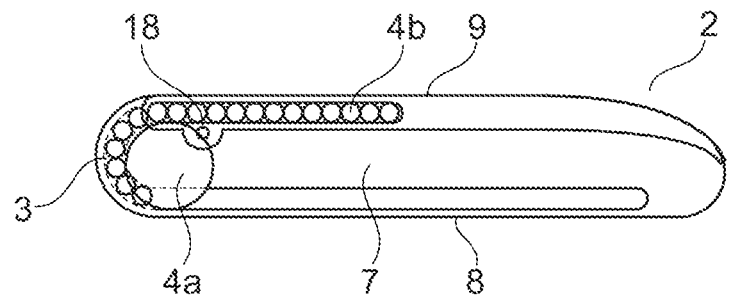
FIGS. 5a to 5d show an embodiment of the apparatus.

In FIG. 5a the housing 2 is closed and the roller arrangement 3 substantially withdrawn from the bottom part 8 and most of the rollers 4b are located in the top part 9 except from the front roller 4a.

The top part 9 is attached to the side part 7 of the housing 2 by means of a rivet 18. The rivet 18 is arranged between the top part 9 and the side parts 7 so the top part can swing around the rivet 18 and function as lid, which can open and close and provide access to the interior of the housing 2. In FIG. 5a the top part 9 is in the closed position.

Figure 5B:
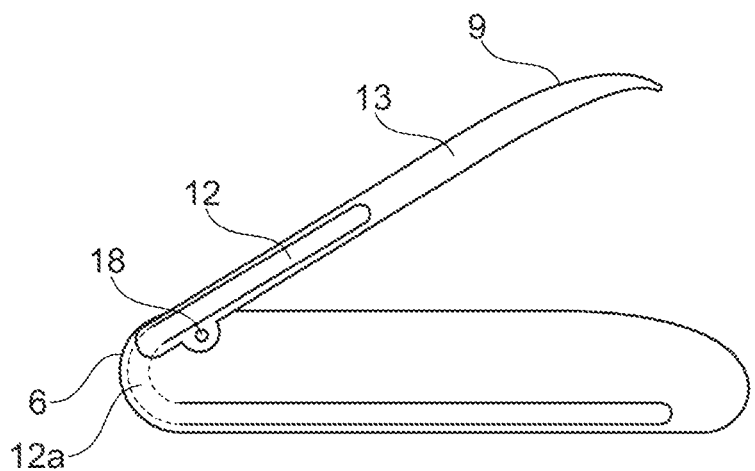

In FIG. 5b the top part 9 is partly opened. The part of the steering track 12a which is located in the rear end 6 of the housing 2 is flexible. Thus, the flexible part 12a indicated with dotted lines of the steering track 12 serves to allow the roller arrangement 3 to move from the steering track located in the top part 9 and mounted on side wall 13 to the steering track mounted on the side part 7 close to the bottom 8 and vice versa.

Figure 5C:
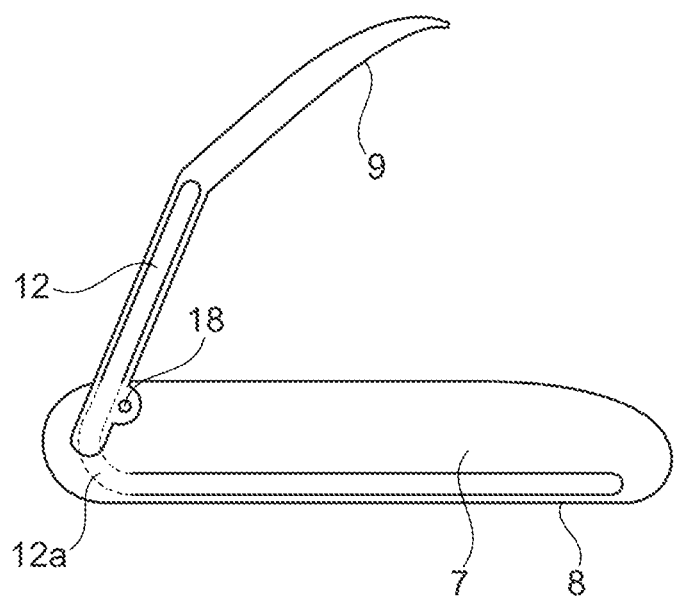

FIG. 5c shows the situation where the top part 9 is in a position where the housing 2 is close to opening. The flexible movement of the flexible part 12a of the steering track is indicated.

Figure 5D:
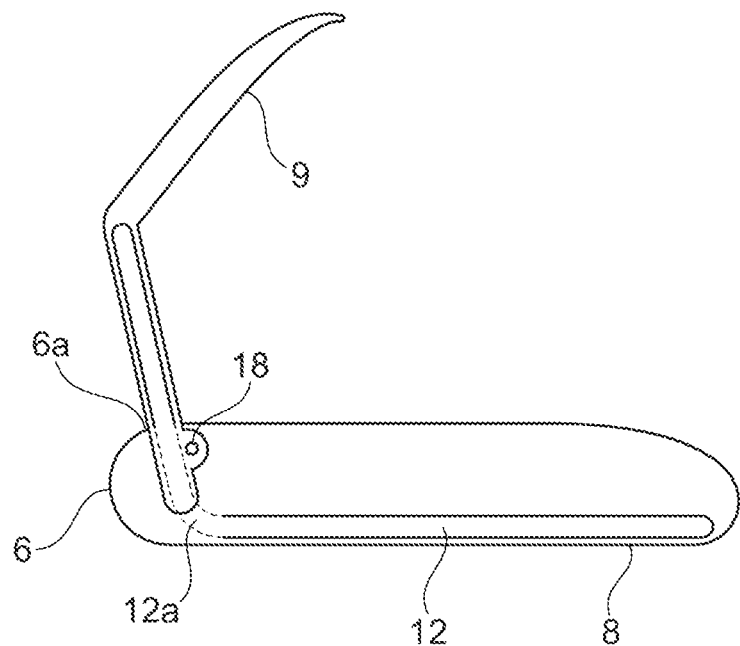

In FIG. 5d the top part 9 is fully opened and further movement of the top part 9 in the direction of the rear end 6 is blocked by a stop 6a.

Figures 6A, 6B:
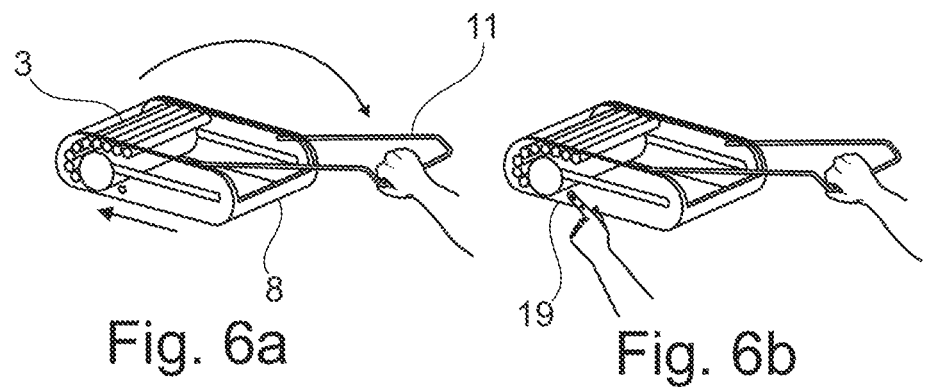
FIGS. 6a to 6h illustrate the function of the apparatus.

The FIGS. 6a to 6b shows how an embodiment of the apparatus IV-GO™ functions and how to place a compressible bag in the apparatus.

In FIG. 6a the operator pulls the handle 11 as indicated by arrow and the roller arrangement 3 is pulled back from the bottom part 8 as indicated by arrow. This operation also puts load on and charges the spring.

In FIG. 6b the operator pushes the control button 19 which will fix the roller arrangement in the position where it is pulled back from the bottom part of the apparatus.

Figures 6C, 6D:
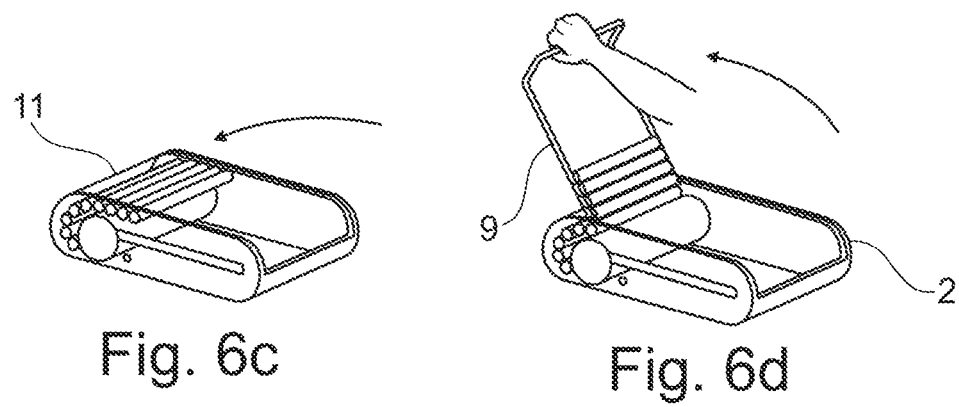

In FIG. 6c the operator swings the handle 11 back as indicated by arrow and opens the top part 9 to provide access to the interior of the housing as shown in FIG. 6d.

The housing 2 is now ready to receive a liquid filled compressible bag 20 which the operator place on the bottom part 8 in the housing 2. This operation in shown in FIG. 6e.

Figures 6E, 6F:
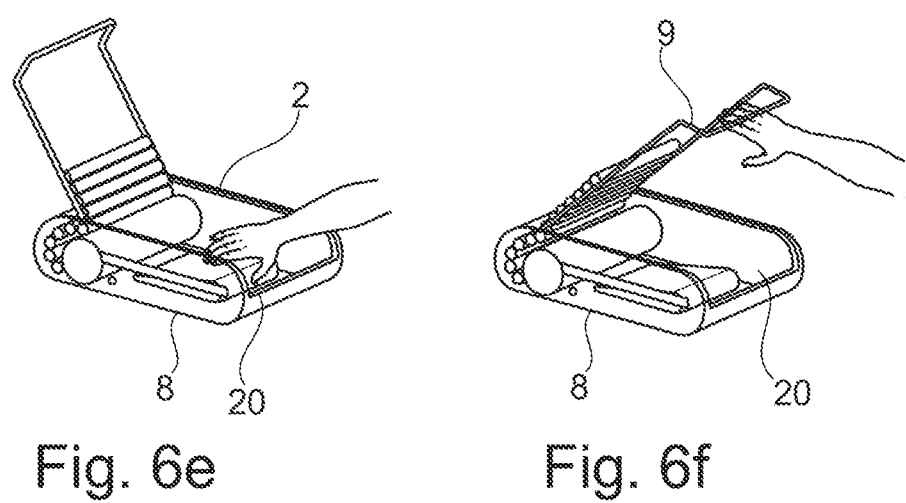

After fixation of the compressible bag on the bottom part 8 of the housing 2 the operator closes the top part 9 as shown in FIG. 6f.

Figure 6G:
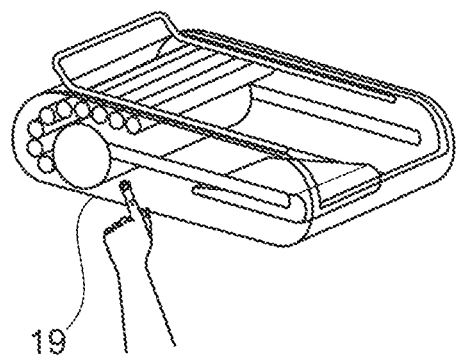

In FIG. 6g the operator again activates the control button 19 and release the roller arrangement.

Figure 6H:
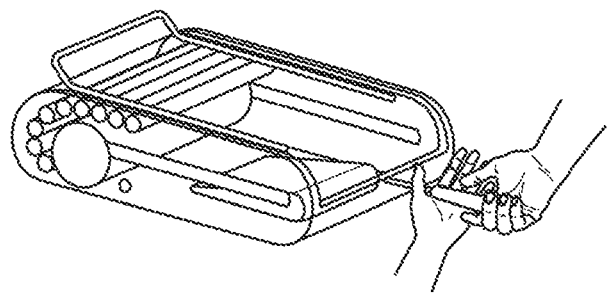

Finally, as shown in FIG. 6h, the operator connects the compressible bag 20 with tubes, which can provide intravenous treatment to a patient.

Figure 7:
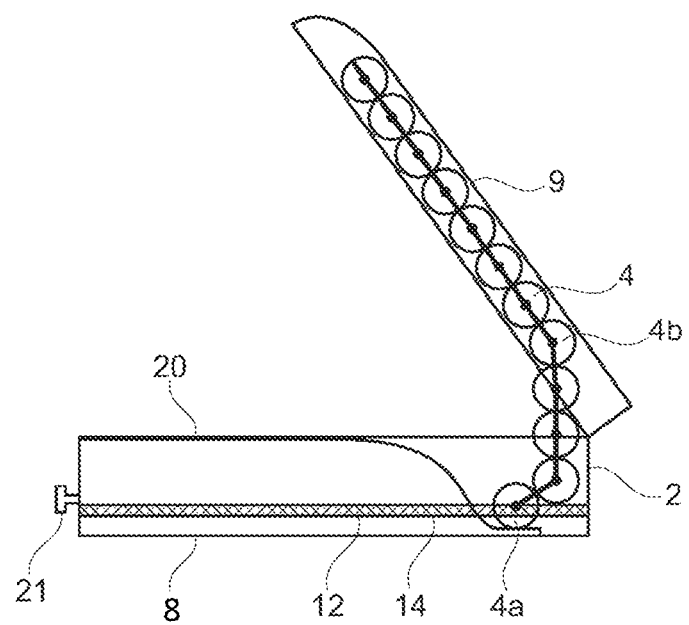
FIG. 7 illustrates a compressible bag in the apparatus.

FIG. 7 shows an embodiment of the apparatus IV-GO™ in which the top part 9 is open and a compressible bag 20 is disposed on the bottom part 9 of the housing 2. The roller arrangement 4 is substantially withdrawn from the bottom part 8 and the major part of the rollers 4b are located in the top part 9. Thus, the liquid filled compressible bag 20 can be disposed easily on the bottom part 8 and in the housing 2.

In this embodiment, the rollers 4a and 4b in the roller arrangement 4 have the same diameter, i.e. the front roller 4a has the same diameter as the follower rollers 4b.

Moreover, in the embodiment shown in FIG. 7 only the front roller 4a is attached to the spring 14, which is located in the steering track 12. However, the front roller 4a is interconnected with the follower rollers 4b by means of a chain 4c, and, in this manner the front roller 4a can drag the follower rollers 4b over bottom part 8 and the compressible bag 20 as shown in FIG. 8.

Figure 8:
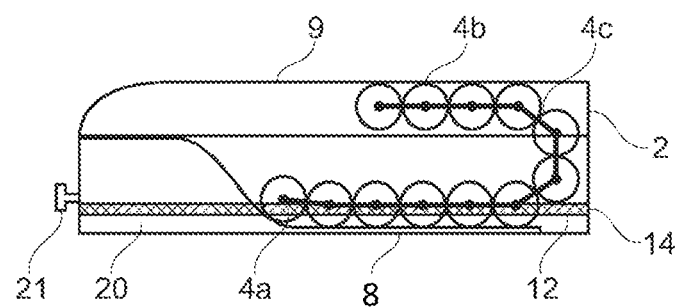
FIG. 8 illustrates how the compressible bag is emptied.

FIG. 8 shows the embodiment of FIG. 7 where the top part 9 is closed and closing the housing 2. The roller arrangement 4 has been released from the top part 9 and the front roller 4a has by means of the spring 14 and chain 4c dragged the follower rollers 4b partly over the bottom part 8 where the roller partly have compressed the compressible bag 20 which has delivered liquid via outlet tube 21.

Figure 9:
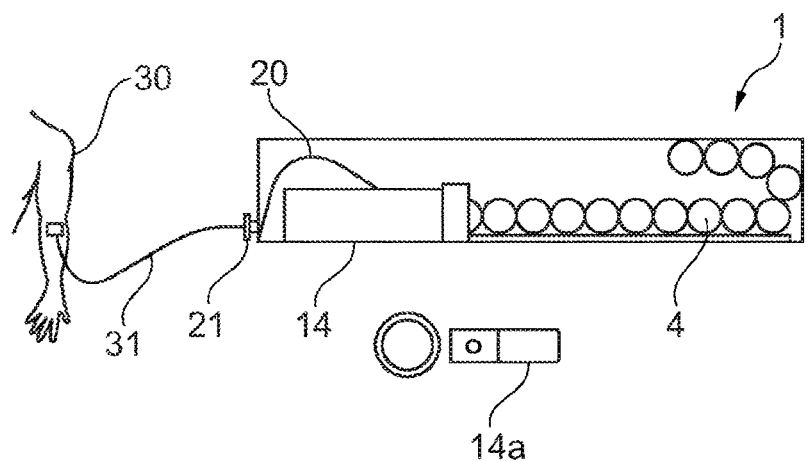
FIG. 9 illustrates an embodiment of the apparatus.

FIG. 9 shows an embodiment of the apparatus 1 where the propulsion of the roller arrangement 4 is provided by a constant-force spring 14. A more detailed view of the constant-force spring is shown with reference number 14a. However, as such constant-force springs are well-known and well-described in technical literature.

In the embodiment shown in FIG. 9 the apparatus 1 is providing intravenous treatment to a patient 30. The patient is connected to the compressible bag 20 with liquid by the outlet tube 21 and tube 31.

Figures 10A, 10B:
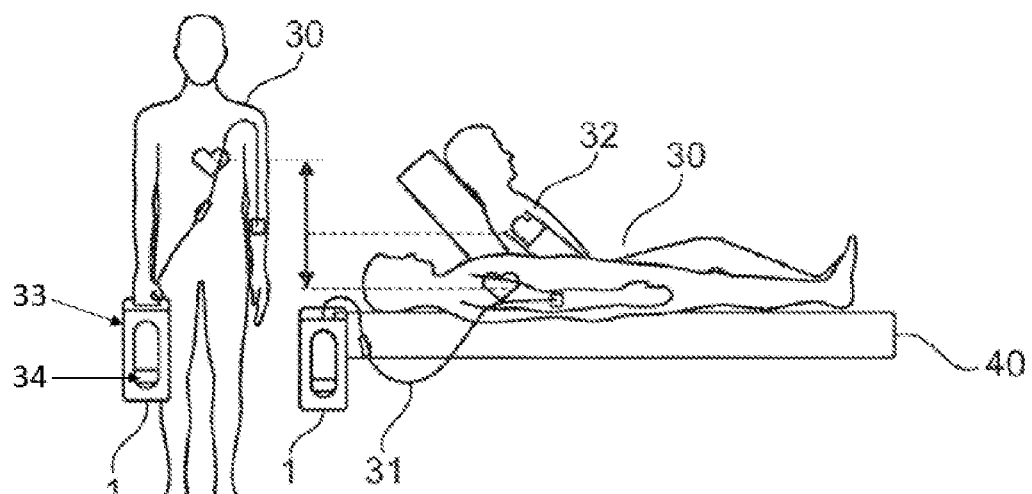
FIGS. 10a to 10b show the apparatus with a patient.

FIGS. 10a to 10b illustrate how the assembly according to the invention can be used in the treatment of a patient without the need of a pole. FIGS. 10a to 10b show the apparatus 1 connected to and providing intravenous treatment to a patient 30 via tube 31. In FIG. 10a the patient 30 is standing and in FIG. 10b the patient 30 is lying on a bed 40.

FIGS. 11a to 11b show the situation of intravenous treatment using a pole 40. The pole 40 comprises a holder 41 for the bag 20 containing the liquid which is dispensed to the patient 30 via the tube 31. As it can be seen, the bag 20 should be disposed well above the level of the heart to provide sufficient pressure by gravity. FIG. 11a shows the patient standing and FIG. 11b shows the patient lying.

However, the present invention as shown in FIGS. 10a to 10b, in both cases, where the patient is standing and the patient is lying, the apparatus 1 is capable of delivering pressurized liquid at a level below the level of the heart 31 of the patient and no pole is required for the treatment.

FIGS. 12a to 12d illustrates yet an embodiment of the invention seen from the top.

Figure 12A:
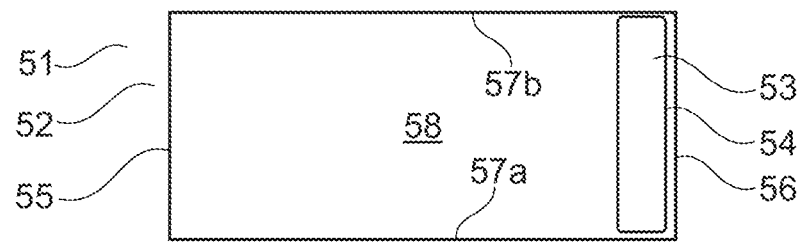
FIGS. 12a to 12d show an embodiment with one roller seen from the top.

FIG. 12a shows the apparatus 51 seen from the top without a compressible bag. The apparatus comprises a housing 52 with a dispensing end 55, a rear end 56, two side parts 57a and 57b and a bottom part 58.

The roller arrangement 53 comprises one roller 54, which in the figure is present in the rear end of the housing 52.

Figure 12B:
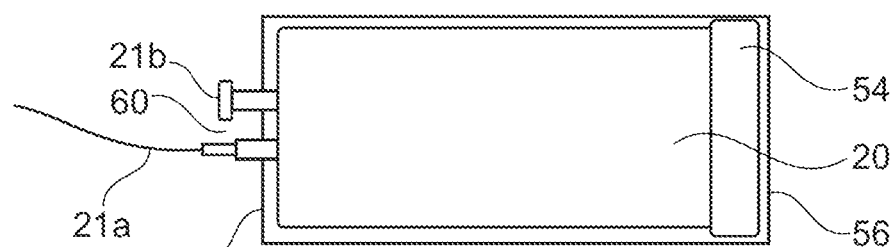
Figure 12C:
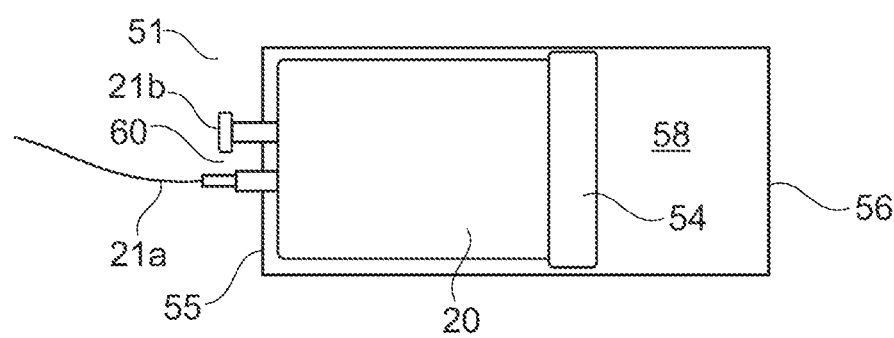

FIG. 12b illustrates the situation where a compressible bag 20 is placed in the housing 52 with the outlet tubes 21a and 21b passing through the opening 60 in the housing. The rear end of the compressible bag is attached to the roller 54, e.g. by means of tape or a squeezing device, such than when the roller 54 moves towards the dispensing end 55 of the housing the compressible bag is rolled up on the roller 54. This situation is illustrated in FIG. 12c where the roller 54 moves towards the dispensing end 55 while the compressible bag 20 at the same time is rolled up on the roller 54.

Figure 12D:
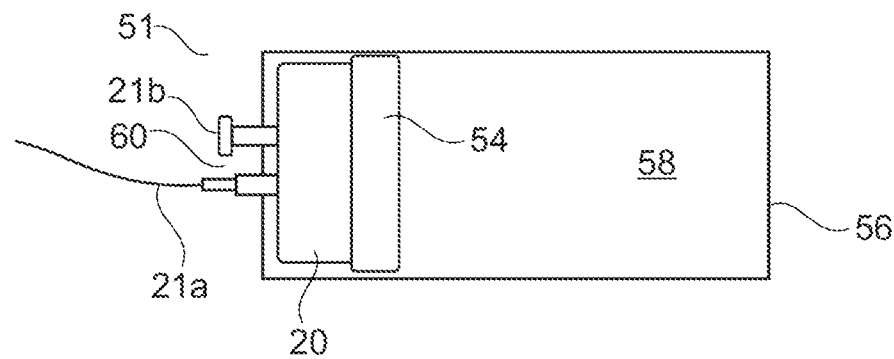

In FIG. 12d the roller 54 has almost reached the dispensing end 55 and most of the compressible bag 20 is rolled up on the roller 54, whereby most of the liquid is dispensed from the bag.

FIGS. 13a to 13d illustrates the apparatus shown in FIG. 12 seen from the side.

Figure 13A:
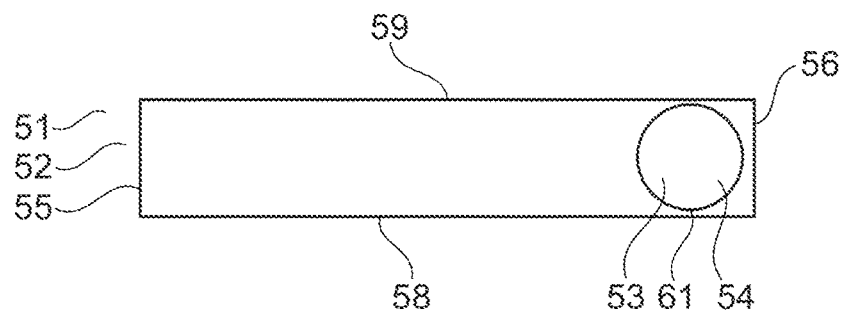
FIGS. 13a to 13d show an embodiment with one roller seen from the side.

In FIG. 13a shows the housing 52 without the compressible bag. The dispensing end 55, the rear end 56, the bottom part 58 and the top part 59 is seen in the figure. The gap 61 between the bottom part 58 and the roller 54 of the roller arrangement 53 is shown.

Figure 13B:
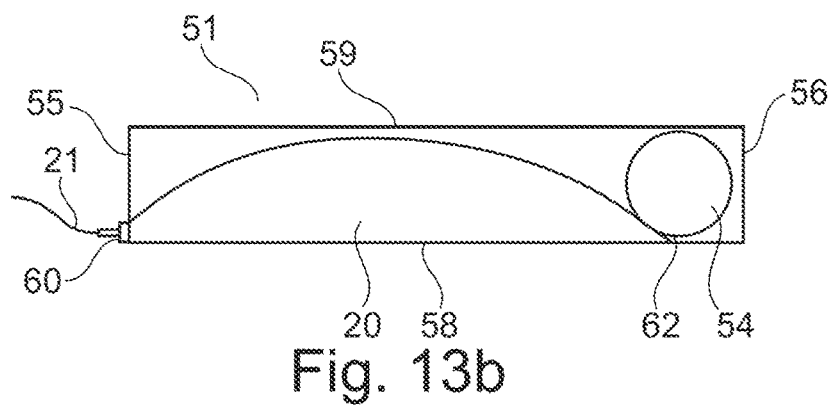

In FIG. 13b corresponding to FIG. 12b the compressible bag 20 has been placed in the housing 52 resting on the bottom part 58 and with its rear end attached to the roller 54 at the surface area 62 of the roller. The outlet tubes 21 pass via opening 60 in the dispensing end through the wall of the dispensing end 55.

Figure 13C:
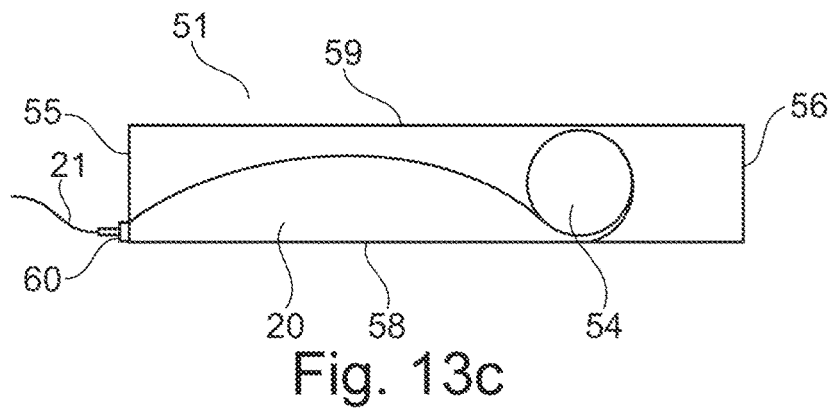

FIG. 13c corresponding to FIG. 12c is the side view where the roller 54 has started moving towards the dispensing end 55. Here it can be seen that the compressible bag 20 is rolled up on the roller 54 during its movement towards the dispensing end 55.

Figure 13D:
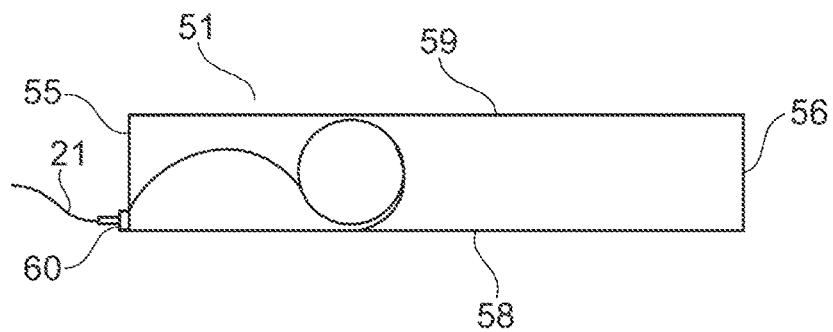

FIG. 13d corresponds to FIG. 12d and shows a side view of the situation where the roller 54 has almost reached the dispensing end.

FIGS. 14a to 14d illustrate an embodiment of the roller arrangement with one roller 54. FIG. 14a show a torsion spring 70, which can be placed on the axle 71 shown in FIG. 14b. Outside the torsion spring 70 the cylinder 72 shown in FIG. 14c and which constitute the outer surface of the roller is placed. The torsion spring 70 is attached to the axle 71 with the end part 70b and to the cylinder 72 by the end part 70a.

FIG. 14d illustrates the assembled parts forming the roller 54. When the roller is mounted in the apparatus the axle 71 is fixed in the steering tracks in such a way that it cannot rotate, but only is able to move in a longitudinal direction between the rear end and the dispensing end of the housing as illustrated above. Thus, by torsion of the cylinder 72 in respect of the axle 71 torque is build up in the torsion spring. This torque is utilized to move the roller 54 from the rear end of the housing towards the dispensing end of the housing and to squeeze out the liquid in the compressible bag.

The roller arrangement has been illustrated as a spring activated roller arrangement, however, electric motors may also be used to activate the rollers.

As mentioned, the figures only illustrate examples and it is clear that the skilled person is able to adapt the apparatus with other features than shown in the figures. The apparatus may e.g., comprise a heating arrangement 34 (FIG. 10a) to keep a desired temperature of the liquid to be dispensed. The apparatus may also comprise a vibrating device 33 (FIG. 10a) which may facilitate the dispensing of a viscous liquid and the apparatus may also comprise a timer device allowing the apparatus to dispense liquid in a predetermined period. The skilled person is also be able to adapt the apparatus to contain two or more bags in the housing, e.g. with the same or different liquids to be dispensed simultaneously or subsequent to each other.

The invention claimed is:

1. An apparatus for dispensing a liquid from a compressible bag, the apparatus comprising:
 a housing with a dispensing end and an opposite rear end, a bottom part and a pair of side parts,
 a roller arrangement and a pair of steering tracks mounted in a track length direction on the pair of side parts, the roller arrangement comprises a front roller with an outer surface, the front roller adapted to roll from the rear end towards the dispensing end,
 wherein a gap is provided between the bottom part and the outer surface of the front roller, the gap is from 2 mm to 10 mm determined where the outer surface of the front roller is closest to the bottom part, and
 wherein the housing is adapted for receiving the compressible bag and wherein the bottom part is adapted for supporting the compressible bag, and
 wherein the front roller comprises a front roller axle oriented perpendicular to the steering tracks and wherein the front roller axle is fixed in the steering tracks such that the front roller axle can move in a longitudinal direction between the rear end and the dispensing end without rotation.

2. The apparatus according to claim 1, wherein the bottom part is planar.

3. The apparatus according to claim 1, wherein the roller arrangement is activated by a spring arrangement.

4. The apparatus according to claim 3, wherein the spring activated roller arrangement comprises the front roller and at least one spring operatively engaged with, operatively connected to, or integrated with the front roller axle forming part of the front roller or being surrounded by a hub of the front roller.

5. The apparatus according to claim 3, wherein said spring activated roller arrangement comprises the front roller, wherein a spring of the spring arrangement is engaged with the pair of tracks to hold the front roller axle perpendicular to the pair of tracks, and
 wherein the front roller has a roller body,
 wherein the outer surface of the front roller is adapted to directly engage with the compressible bag placed on the bottom part as the spring moves the front roller of the roller arrangement over the bottom part towards the dispensing end.

6. The apparatus according to claim 5, wherein the spring is at least partly integrated in the front roller.

7. The apparatus according to claim 1, wherein the roller arrangement is activated by a pulling or drawing device.

8. The apparatus according to claim 7, wherein the pulling or drawing device is electrically powered.

9. The apparatus according to claim 7, wherein the pulling or drawing device is arranged in the front roller.

10. The apparatus according to claim 7, wherein the pulling or drawing device is arranged exterior to the front roller.

11. The apparatus according to claim 1, wherein the apparatus comprises a control device configured for assisting dispensing of a liquid.

12. The apparatus according to claim 11, wherein the control device comprises an electronic device for monitoring at least one condition of the compressible bag arranged in the housing of the apparatus.

13. The apparatus according to claim 11, wherein the control device is adapted for monitoring at least one condition, wherein the at least one condition comprises at least one dispensing condition selected from the group of dispensing rate, dispensing status and dispensing time left.

14. The apparatus according to claim 11, wherein the control device comprises a heating arrangement adapted to heat the liquid in the compressible bag.

15. The apparatus according to claim 11, wherein the control device comprises a vibrating device adapted to facilitate dispensing of a liquid.

16. The apparatus according to claim 11, wherein the control device comprises a timer device configured to interrupt the roller arrangement after a predetermined period.

17. The apparatus according to claim 11, wherein the control device is configured for controlling the movement of the roller arrangement.

18. The apparatus according to claim 1, wherein the front roller comprises a cylinder, wherein the cylinder constitutes the outer surface of the front roller.

* * * * *